United States Patent [19]

Michel et al.

[11] Patent Number: 4,910,175

[45] Date of Patent: Mar. 20, 1990

[54] CATALYST RECOVERY

[75] Inventors: Robert E. Michel; Matthew R. Kegelman, both of Wilmington, Del.; Frederick J. Sebelist, Hendersonville, Tenn.

[73] Assignee: E. I. Du Pont de Nemours and Company, Wilmington, Del.

[21] Appl. No.: 283,160

[22] Filed: Dec. 12, 1988

[51] Int. Cl.[4] .......................... B01J 38/68; B01J 31/40; C07C 51/265
[52] U.S. Cl. ............................. 502/24; 502/28; 556/49; 556/149; 562/412; 562/414
[58] Field of Search ............. 502/24, 28; 562/412, 562/414; 556/49, 149; 423/140

[56] References Cited

U.S. PATENT DOCUMENTS

| 3,673,154 | 6/1972 | Trevillyan | 423/140 |
| 3,840,469 | 10/1974 | Hobbs, Jr. et al. | 502/24 |
| 4,459,365 | 7/1984 | Suzuki et al. | 562/414 |
| 4,488,999 | 12/1984 | Feld | 502/24 |
| 4,490,297 | 12/1984 | Feld et al. | 556/149 |
| 4,490,298 | 12/1984 | Feld | 562/414 |
| 4,587,355 | 5/1986 | Brown et al. | 562/414 |
| 4,769,488 | 9/1988 | Howicki et al. | 562/414 |
| 4,786,752 | 11/1988 | Holzhauer et al. | 502/28 |

Primary Examiner—Paul E. Konopka

[57] ABSTRACT

Recovery of cobalt and manganese catalyst from oxidation process, by precipitation with oxalic acid and alkali metal hydroxide, followed by oxidation of the precipitate in acetic acid to form cobalt and manganese acetate.

5 Claims, 1 Drawing Sheet

CONTINUOUS OXILATE PRECIPITATION
EXPERIMENTAL APPARATUS

CONTINUOUS OXILATE PRECIPITATION
EXPERIMENTAL APPARATUS
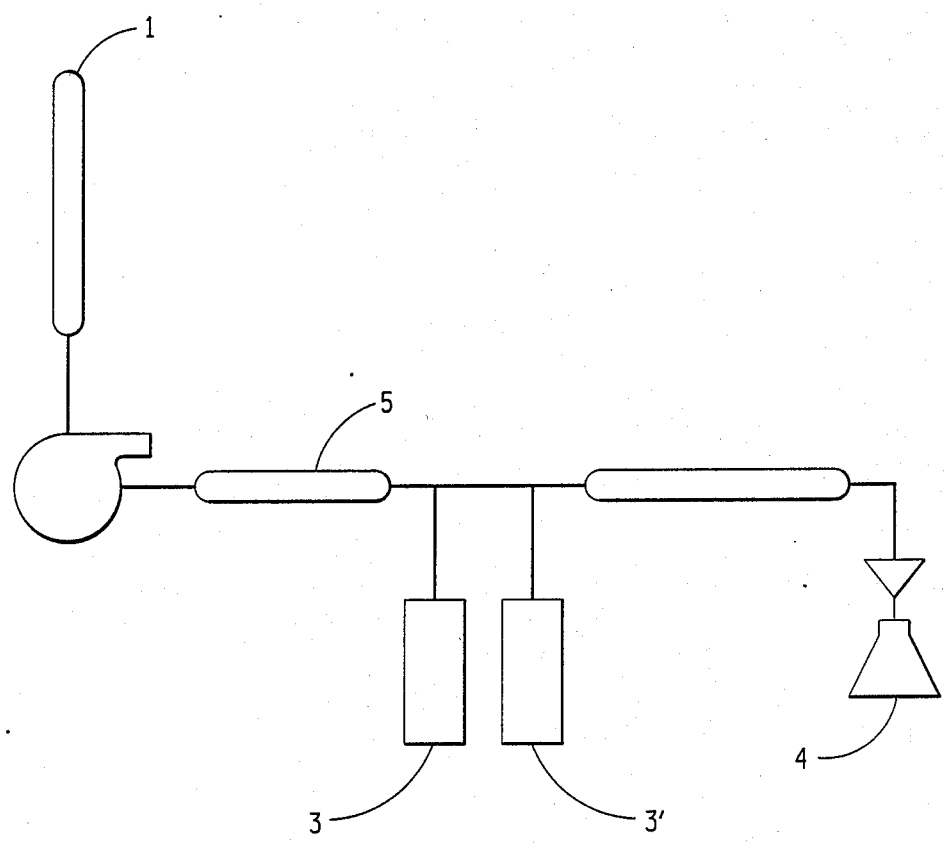

CATALYST RECOVERY

FIELD OF THE INVENTION

This invention relates to a process for the recovery of and regeneration of cobalt and manganese catalyst components from a mother liquor containing these components and corrosion metal compounds of iron and nickel. The process is particularly concerned with recovering and regenerating catalyst components from a mother liquor produced in the oxidation of an alkyl aromatic compound to an alkyl aromatic acid in an acetic acid solvent, and purging corrosion metal compounds of iron and nickel from the mother liquor.

BACKGROUND OF THE INVENTION

Processes for the recovery of metal catalysts components from the mother liquor used in the oxidation of alkyl aromatic compounds such as meta and para-xylenes to isophthalic or terephthalic acid are described in U.S. Pat. Nos. 3,673,154, 3,840,469 and 4,490,297. In the '469 patent and the '297 patent the desired metals are precipitated as oxalate compounds. In the '154 patent the desired metal is precipitated as the carbonate compound. Both the '154 patent and the '469 patent refer to the problem of tramp and/or corrosion metals (iron, nickel and chromium) and include suggestions as to how to separate these metals from the desired metals. In '469 it is found that the tramp or corrosion metals do not precipitate simultaneously with the cobalt, while in '154, the iron and chromium are precipitated first by a pH adjustment. In the '469 patent the catalyst, cobalt acetate, is regenerated by mixing the cobalt oxalate in acetic acid with calcium ions. In the '154 patent the catalyst, cobalt acetate is regenerated by mixing the cobalt carbonate with an excess of acetic acid and heating. In the '297 patent the catalyst is regenerated by reacting the cobalt oxalate in acetic acid with acetyl bromide and/or hydrogen bromide.

It is an object of this invention to provide a process for the recovery of cobalt and manganese catalyst components from an acetic acid mother liquor, and lower the level of corrosion and/or trash metals in the catalyst and separating acetic acid from the mother liquor.

SUMMARY OF THE INVENTION

The present invention is a process for the recovery and regeneration of cobalt catalyst and manganese catalyst from a mother liquor containing acetic acid, cobalt compounds, manganese compounds, and corrosion metal compounds of iron and nickel, said mother liquor having been produced by the use of cobalt catalysts and manganese catalyst in the oxidation of an alkyl aromatic compound to form an alkyl aromatic acid in an acetic acid containing solvent which comprises: (a) precipitating cobalt and manganese from the mother liquor by the addition of (1) oxalic acid and alkali metal hydroxide the amount of alkali metal hydroxide being at least about equal on a molar basis to the amount of oxalic acid, or (2) monoalkali metal oxalate, (b) isolating the precipitate, (c) dispersing the precipitate in a solution containing aqueous acetic acid (d) and forming cobalt acetate and manganese acetate by oxidizing the oxalic acid moiety to carbon oxides. The cobalt and manganese oxalates, may be separated from the other components of the mother liquor by filtration. Preferably ketone is present in acetic acid dispersion that is oxidized to form cobalt acetate and manganese acetate. The mother liquor after isolation of the precipitate is preferably subjected to evaporation to recover the acetic acid component.

The process is especially useful to recover and recycle cobalt and manganese components in a process for the preparation of terephthalic acid by the oxidation of para-xylene or in the preparation of isophthalic acid by the oxidation of meta-xylene.

DETAILED DESCRIPTION

The FIGURE is of the apparatus employed to carry out the examples.

In the oxidation of alkyl aromatic compounds such as para-xylene to form aromatic acids such as terephthalic acid, it is conventional to carry out the oxidation by passing a gaseous oxygen source (often air) through an acetic acid mother liquor containing the alkyl aromatic compound and dissolved catalytic amounts of cobalt and manganese acetate. Such process are often operated continuously, and the mother liquor containing the reaction product is continuously removed from the reactor, the desired aromatic acid separated, and the mother liquor containing the dissolved catalysts returned to the reactor along with more alkyl aromatic compound. After a time the stream becomes contaminated with corrosion metals and/or tramp metals such as iron, nickel and chromium, as well as undesired organic reaction products and the desired aromatic acid may not be as pure as required. Because the cobalt and manganese components of the mixture are relatively expensive it is desirable that these components be recovered from the circulating mother liquor. It is also desirable to remove the corrosion/tramp metals and undesired organic reaction products from the circulating mother liquor.

When the mother liquor is treated with oxalic acid and alkali metal hydroxide or monoalkali metal oxalate, cobalt forms the most insoluble oxalate in the mixture and thus is precipitated preferentially. Some manganese is also precipitated.

The precipitated oxalates are separated from the mother liquor, for example by filtration. The oxalate precipitate is then mixed with (dispersed in) aqueous acetic acid. Preferably an oxygen containing gas is mixed with the dispersion while the dispersion is heated. The cobalt and manganese oxalates dissolve, and cobalt and manganese acetates form. The oxalate moiety is oxidized to carbon oxides. The solution containing the cobalt acetate and the manganese acetate may now be mixed with alkyl aromatic compound, e.g. para-xylene, and that mixture oxidized to form aromatic acid, e.g. terephthatic acid.

If desired the precipitated oxalates may be added as solids to the alkyl aromatic oxidation reactor containing aqueous acetic acid, the alkyl aromatic compound and the oxidizing gas. The cobalt and manganese oxalates are converted to cobalt and manganese acetate and the oxalate moiety is oxidized to carbon oxides, while the alkyl aromatic compound is being oxidized.

The filtrate (the mother liquor minus the precipitated cobalt and manganese oxalate) may be evaporated to recover the acetic acid portion of the liquor, and the residual, containing iron, and nickel components as well as undesirable organic reaction products, may be burned or disposed of in some other manner.

It is sometimes desirable to add about 0.5 to 3% by weight of ketone or aldehyde to the solvent (aqueous acetic acid) that is used to recover the cobalt and manganese components from the precipitated oxalates. The ketone or aldehyde speeds up the conversion of the oxalates to the acetates. Suitable ketones and aldehydes include those with active α-hydrogens such as methyl ethyl ketone, methyl isobutyl ketone, and acetaldehyde.

The addition of alkali metal hydroxide to the oxalic acid improves the purge of iron and nickel from the mother liquor, in other words this addition results in less iron and nickel precipitating with the cobalt and manganese oxalates. Monoalkali metal oxalate achieves the same result. The addition of alkali metal or monoalkali metal oxalate also gives the desirable result of lowering the amount of free oxalic acid present in the solution, and reduces the amount of corrosion that is produced in the reactors.

The effect of base, expressed as Na, to oxalate molar ratio is demonstrated by comparing runs 1, 2 and 3; 7 and 8; 9 and 10; 18 and 19; and 21 and 23.

Demonstration of the conversion of the catalyst oxalates to useful acetates was carried out in a stirred one liter titanium autoclave. The results of these experiments are shown in Table II. The data definitely show that the presence of oxygen is beneficial for conversion of the oxalates. They also show the beneficial effect of ketone addition to the process.

TABLE I

RECOVERY OF COBALT AND MANGANESE AS OXALATES (1)

| Run | SOURCE | Co (ppm) | Mn (ppm) | Fe (ppm) | Ni (ppm) | Oxalate/Metal | Na/Oxalate | Co (%) | Mn (%) | Fe (%) | Ni (%) | Addition Order (2) |
|---|---|---|---|---|---|---|---|---|---|---|---|---|
| 1 | Synth. | 225 | 509 | 39 | 20 | 0.51 | 1.00 | 75.1 | 16.4 | 80.0 | 15.0 | 1 |
| x2 | Synth. | 225 | 509 | 39 | 20 | 0.51 | 0.50 | 71.6 | 17.3 | 54.7 | 17.5 | 1 |
| x3 | Synth. | 225 | 509 | 39 | 20 | 0.51 | 0.00 | 69.2 | 11.6 | 64.0 | 20.0 | 1 |
| 4 | Synth. | 396 | 369 | 0 | 1 | 1.00 | 2.25 | 97.9 | 81.0 | 66.7 | 1.7 | 3 |
| 5 | Synth. | 225 | 519 |   |   | 1.03 | 1.00 | 98.2 | 82.0 |   |   | 1 |
| 6 | Synth. | 225 | 509 | 39 | 20 | 1.03 | 1.00 | 99.1 | 68.6 | 70.0 | 3.0 | 1 |
| 7 | Synth. | 225 | 509 | 39 | 20 | 1.03 | 1.00 | 99.2 | 76.4 | 75.0 | 4.0 | 1 |
| x8 | Synth. | 225 | 509 | 39 | 20 | 1.03 | 0.50 | 98.9 | 59.6 | 30.7 | 1.5 | 1 |
| x9 | Synth. | 225 | 519 |   |   | 1.03 | 0.00 | 98.5 | 69.2 |   |   | 1 |
| x10 | Synth. | 225 | 509 | 39 | 20 | 1.03 | 0.00 | 99.0 | 57.2 | 23.0 | 2.0 | 1 |
| 11 | Synth. | 225 | 509 | 39 | 20 | 1.12 | 2.25 | 99.8 | 97.2 | 71.6 | 1.5 | 3 |
| 12 | M.L. (3) | 333 | 605 | 6 | 2 | 0.42 | 1.00 | 47.1 | 14.0 | 79.0 | 44.5 | 1 |
| 13 | M.L. (3) | 333 | 685 | 6 | 2 | 0.78 | 1.00 | 71.5 | 58.8 | 69.1 | 18.2 | 1 |
| 14 | M.L. (3) | 221 | 589 | 14 |   | 1.06 | 1.00 | 97.7 | 90.7 | 96.4 |   | 1 |
| x15 | M.L. (3) | 221 | 589 | 14 |   | 1.06 | 0.00 | 99.1 | 97.1 | 55.5 |   | 1 |
| 16 | M.L. (3) | 333 | 685 | 6 | 2 | 1.55 | 1.00 | 99.8 | 99.5 | 70.9 | 3.6 | 1 |
| 17 | M.L. (3) | 193 | 468 | 3 |   | 1.77 | 1.00 | 99.8 | 99.7 | 90.0 |   | 1 |
| x18 | M.L. (3) | 193 | 468 | 3 |   | 1.77 | 0.50 | 99.8 | 99.4 | 63.3 |   | 1 |
| x19 | M.L. (3) | 193 | 468 | 3 |   | 1.77 | 0.00 | 99.5 | 98.3 | 33.3 |   | 1 |
| 20 | M.L. (3) | 253 | 275 | 4 | 3 | 2.05 | 2.25 | 99.5 | 98.1 | 80.5 | 2.0 | 3 |
| 21 | M.L. (3) | 221 | 589 | 14 |   | 2.11 | 1.00 | 99.9 | 99.8 | 84.8 |   | 1 |
| x22 | M.L. (3) | 221 | 589 | 14 |   | 2.11 | 0.00 | 99.9 | 96.6 | 28.6 |   | 1 |

(1) Hold-up time = 5 sec., addition until filtration
(2) Addition order 1 = NaOH ahead of oxalate
(2) Addition order 2 = Sodium oxalate added
(2) Addition order 3 = oxalate ahead of NaOH
(3) Plant mother liquor purge
X These run (marked with an X are not examples of the invention - the Na/oxalate ratio is lower than about 1 and accordingly the purge of iron and/or nickel was unsatisfactory.

EXAMPLES

The continuous experiments were carried out using the apparatus detailed in the FIGURE. The flow rate of the catalyst containing aqueous acetic acid contained in reservoir 1 was set at 10 ml/min. Variable flow high pressure syringe pumps 3 and 3' were used to supply a saturated aqueous solution of oxalic acid and an aqueous solution of 5% NaOH. In a few cases a single pump was used and monosodium oxalate solution was fed. The preheater 5 was set at 100° C., and the steam jacketed reactor was operated at 100° C. The time between oxalate addition and the filtration step was 5 sec. Filtration was accomplished at filter 4 using a glass fiber paper of 1.5 micron retention capability. Experiments involving both synthetic and authentic oxidation mother liquor samples were run in order to investigate the effect that both the oxalate to metals and the sodium hydroxide to oxalate ratios would have on the recovery of catalyst and the purge of corrosion products. The results are presented in Table I.

TABLE II

RECOVERY OF COBALT AND MANGANESE OXALATES(1)

| Run | Temp. (C.) | Time. (min.) | O$_2$ (2) | Ketone (3) | % Co | % Mn |
|---|---|---|---|---|---|---|
| 1 | 150 | 10 | NO | NO | 0 | 16 |
| 2 | 150 | 10 | YES | YES | 15 | 36 |
| 3 | 150 | 30 | YES | NO | 12 | 81 |
| 4 | 150 | 30 | YES | YES | 93 | 90 |
| 5 | 150 | 120 | YES | NO | 95 | 100 |
| 6 | 200 | 30 | NO | NO | 4 | 24 |
| 7 | 200 | 30 | YES | NO | 91 | 85 |
| 8 | 200 | 30 | YES | YES | 94 | 90 |

(1) 7.0 grams of mixed 1/1 Co/Mn oxalates in 200 ml of 85% HOAc. Total pressure = 300 psig.
(2) 5% O$_2$ in N$_2$
(3) 1% methyl ethyl ketone based on total solvent

We claim:
1. A process for the recovery and regeneration of cobalt catalyst and manganese catalyst from a mother liquor containing acetic acid, cobalt compounds, manganese compounds, and corrosion metal compounds of iron and nickel, said mother liquor having been produced by the use of cobalt catalysts and manganese catalyst in the oxidation of an alkyl aromatic compound to form an alkyl aromatic acid in an acetic acid containing solvent, which comprises: (a) precipitating cobalt and manganese from the mother liquor by the addition of (1) oxalic acid and alkali metal hydroxide, the amount of alkali metal hydroxide being about equal on a molar basis to the amount of oxalic acid, or (2) monoalkali metal oxalate, (b) isolating the precipitate, (c) dispersing the precipitate in a solution containing aqueous acetic acid (d) and forming cobalt acetate and manganese acetate by oxidizing the oxalic acid moiety to carbon oxides.

2. The process of claim 1 in which the precipitated cobalt and manganese compounds are cobalt and manganese oxalate, and in which the compounds are separated from the other components of the mother liquor by filtration.

3. The process of claim 1 in which a ketone or an aldehyde is present in acetic acid dispersion that is oxidized to form cobalt acetate and manganese acetate.

4. The process of claim 1 in which the mother liquor after separation of the precipitate is subjected to evaporation to recover the acetic acid.

5. The process of claim 1 in which the alkali metal hydroxide is sodium hydroxide, or the monoalkali metal oxalate is monosodium oxalate.

* * * * *